US009481632B1

(12) United States Patent
O'Lenick et al.

(10) Patent No.: US 9,481,632 B1
(45) Date of Patent: Nov. 1, 2016

(54) TOTALLY RANDOMIZED TRANS FAT FREE BUTTERS

(71) Applicants: Thomas George O'Lenick, Dacula, GA (US); Andrew James O'Lenick, Dacula, GA (US)

(72) Inventors: Thomas George O'Lenick, Dacula, GA (US); Andrew James O'Lenick, Dacula, GA (US)

(73) Assignee: SURFATECH CORPORATION, Lawrenceville, GA (US)

( * ) Notice: Subject to any disclaimer, the term of this patent is extended or adjusted under 35 U.S.C. 154(b) by 0 days.

(21) Appl. No.: 14/545,107

(22) Filed: Mar. 27, 2015

(51) Int. Cl.
*C11C 3/00* (2006.01)
*C07C 69/604* (2006.01)

(52) U.S. Cl.
CPC .................................. *C07C 69/604* (2013.01)

(58) Field of Classification Search
CPC .................................................. C07C 69/604
USPC ................................................. 554/169, 227
See application file for complete search history.

(56) References Cited

U.S. PATENT DOCUMENTS 6,013,818 A 1/2000 O'Lenick
6,258,965 B1 7/2001 O'Lenick

*Primary Examiner* — Deborah D Carr

(57) ABSTRACT

Butters are a specific class of cosmetic triglycerides that provide a unique feel on skin. There are very few such materials in nature. In order for a butter to be of interest to the personal care market, it must be (1) soft at room temperature; (2) must not "crack" when handled; (3) must be able to be applied to the skin at ambient temperature by rubbing; (4) must liquefy upon rubbing, (5) must be free of rancidity and (6) must be free of trans acids that are the result of partial hydrogenation. For unsaturated oils to be made into butters, partial hydrogenation is the most common approach. This results in the formation of trans acids which are highly undesirable.

The present invention discloses a series of non-hydrogenated butters made by a process referred to as totally randomized triglycerides. The butters are made using a very specific range of very specific types and ratios of fatty acids to glycerin to provide the highly desirable cosmetic butters meeting the requirements 1-5 above.

20 Claims, No Drawings

TOTALLY RANDOMIZED TRANS FAT FREE BUTTERS

GOVERNMENT SPONSORSHIP

None

FIELD OF THE INVENTION

The present invention is directed to a series of butters that (1) have been prepared using a process that totally randomizes the alkyl distribution in the molecule, and (2) contain very specific amounts and types of fatty acids to produce complex compositions that provide a cosmetically elegant buttery feel on skin.

Butters of this type, unlike those made by hydrogenation of unsaturated triglycerides are free of trans fats, a material that is being regulated in foods by the Food and Drug Administration (FDA). Trans-fats or synthetic fats can be absorbed by the skin and enter the blood stream.

BACKGROUND OF THE INVENTION

The terms oils, fats, butters and waxes have been misused over the years. The historical definition of wax has previous been given. Butters, oils and fats are all triglycerides. Typically a titer point is used to characterize triglycerides. Titer point is very similar to melt point, but is much broader. Due to this wide melting range, it is possible to hold a triglyceride at a specific temperature and have some of the more solid components separate out. Thus the term "titer point" simply refers to the cloudiness that occurs as the lower melting portions start becoming liquid. In direct contrast to a natural triglyceride, a glycerin triester will have a very sharp melt point, typically around 3 degrees from when it starts sweating to when it completely liquefies. Typically they are divided into categories based on their physical nature. Since typically naturally derived triglycerides are specific mixtures of fatty groups, they are characterized by their titer point. Fats have a titer point of over 40.5° C., oils have a titer point of below 40.5° C. Butters have a titer below 40.5° C. but above 20° C. Oils are liquid at room temperature and we now use this word to describe any compound that is a liquid and is insoluble in water.

Butters are very specific triglycerides that are very desirable in the personal care market because they are soft semisolids, liquefy under pressure and provide a cosmetically pleasing feel on the skin. In nature there are basically two butters, coco butter and shea butter. The two butters have the same distribution of alkyl groups, but the position on which the groups are placed by enzymes accounts for the difference between the two.

Triglycerides are the tri-esters of glycerin with three equivalents of organic acid. Fatty acids are defined as those acids having alkyl or alkylene groups being C-5 and higher. The classical organic reaction follows it generally occurs at a temperature of between 150 and 200° C.

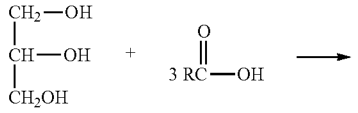

Glycerin

-continued

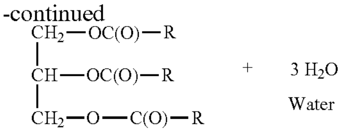

Triglyceride

Water

Having to reach a temperature of 150-180° C. is impossible for living organisms as water would boil and the organisms would die. Living systems perform this chemistry at 37° C. using enzymes. Enzymes are macromolecular biological catalysts. They are responsible for thousands of metabolic processes that sustain life. There is an extraordinary amount of specificity to the way the enzyme systems work. In fact enzymes are so specific, that in 1894 Emil Fischer stated that both the enzyme and the substrate possess specific complementary geometric shapes that fit exactly into one another. This is often referred to as "the lock and key" model.

All living systems have the ability to synthesize triacylglycerols, and the process has been studied intensively in plants and animals especially. Many cell types and organs have the ability to synthesize triacylglycerols, but in animals the liver, intestines and adipose tissue are most active with most of the body stores in the last (see our web page on triacylglycerol composition). Within all cell types, even those of the brain, triacylglycerols are stored as cytoplasmic 'lipid droplets' (also termed 'fat globules', 'oil bodies', 'lipid particles', 'adiposomes', etc) enclosed by a monolayer of phospholipids and hydrophobic proteins, such as the perilipins in adipose tissue or oleosins in seeds. These lipid droplets are now treated as distinctive organelles, with their own characteristic metabolic pathways and associated enzymes—no longer boring blobs of fat. They are not unique to animals and plants as Mycobacteria and yeasts have similar lipid inclusions.

The lipid serves as a store of energy, which can be released rapidly on demand, and as a reserve of essential fatty acids and precursors for eicosanoids. However, lipid droplets may also serve as a protective agency to remove any excess of biologically active and potentially harmful lipids such as free fatty acids, diacylglycerols, cholesterol (as cholesterol esters), retinol esters and coenzyme A esters.

Two main biosynthetic pathways are known, the sn-glycerol-3-phosphate pathway, which predominates in liver and adipose tissue, and a monoacylglycerol pathway in the intestines. In maturing plant seeds and some animal tissues, a third pathway has been recognized in which a diacylglycerol transferase is involved. Triacylglycerol biosynthesis in plants is discussed in greater detail in a separate webpage on this site. The most important route to triacylglycerol biosynthesis is the sn-glycerol-3-phosphate or Kennedy pathway illustrated below, first described by Professor Eugene Kennedy and colleagues in the 1950s, by means of which more than 90% of liver triacylglycerols are produced.

The result of enzymatic biosynthesis is that each hydroxyl group on the glycerin is very specifically substituted by a controlled reaction in which a very specific fatty group is added.

As stated there are two natural butters. Synthetic butters or trans-fats are made by a synthetic or not natural method. Most synthetic butters sold into the personal care market are the result of partial hydrogenation. Any natural oil that contains unsaturation, can be made into a butter by partial hydrogenation. Soybean oil, olive oil or other unsaturated oils when hydrogenated are hardened to provide a mixed saturated/unsaturated product. Therefore in must be clear that most synthetic butters sold in the personal care market are the fruit of partial hydrogenation. Partial hydrogenation is very undesirable due to the fact that: The product contains some unsaturation, either a single unsaturation or two unsaturated groups. The presence of the unsaturation makes the triglyceride susceptible to oxidation in a process called rancidity. Rancidity breaks the double bond into aldehydes having half the molecular weight as the starting material. The resulting aldehyde has an unpleasant aroma and is unacceptable in cosmetic products. Triglycerides that undergo this process are said to be rancid. Rancidification is the process that causes a substance to become rancid, that is, having a rank, unpleasant smell or taste. Specifically, it is the autoxidation of fats into short-chain aldehydes and ketones, which are objectionable in taste and odor.

A major health concern during the partial hydrogenation process is the production of trans fats. Trans fats are the result of a side reaction with the catalyst of the hydrogenation process. This is the result of an unsaturated triglyceride (also called fat), which is normally found as a cis isomer converts to a trans isomer of the unsaturated fat. Isomers are molecules that have the same molecular formula but are bonded together differently. Focusing on the Sp2 double bonded carbons, a cis-isomer has the hydrogen atoms on the same side. Due to the added energy from the hydrogenation process, the activation energy is reached to convert the cis isomers of the unsaturated fat to the thermogenically favored trans isomer of the unsaturated fat. The effect is putting one of the hydrogen atom on the opposite side of one of the carbons. This results in a trans configuration of the double bonded carbons. The human body doesn't recognized trans fats.

While the digestive system treats hydrogenated fats as food, the bloodstream cannot use it. The cells simply try to store the trans fats and deposits them on the artery walls. Ironically, fat that has been completely hydrogenated does not actually contain trans fat; only the partially hydrogenated oil has been shown to cause arterial buildup. However, full hydrogenation makes the oil so hard that it is not usable on its own.

Because they are not metabolized, Trans fats have been linked to an increased risk of coronary heart disease, in which plaque builds up inside the arteries and may cause a heart attack.

The FDA can act when it believes a food ingredient is, in fact, not GRAS (Generally regarded as safe). And that's what the agency's preliminary determination is doing now with partially hydrogenated oils. A Federal Register notice was published on Nov. 7, 2013 announcing the preliminary determination that partially hydrogenated oils are not GRAS, which includes the opening of a 60-day public comment period.

If FDA makes a final determination that PHOs as foods are not GRAS, the agency and food industry would have to figure out a way to phase out the use of PHOs over time. To help address this concern in an appropriate manner, the Federal Register notice calls for comment on how long it would take the food industry to phase out its use of PHOs.

There is ample literature to suggest that trans fats that are applied to the skin will undergo an enzymatic reaction releasing trans fatty acids which as far back as 1989 have been identified as skin penetration enhancers. (Pharm Res 1989 Mar. 6(3): 244-7). This study found that there was "no significant difference between cis and trans unsaturated C16-C18 fatty acid isomers in their effects on naloxone flux, and that all unsaturated fatty acids are more effective enhancers than the corresponding saturated isomers".

Food Chemistry 81 (2003)453-456 discloses that partial hydrogenation of soybean oil results in around 7% trans isomer.

While the FDA currently limits it's activities to food, it makes little sense to apply of butters containing trans fats to the skin.

An article entitled transcutaneous absorption of topically massaged oil in neonates published in the Indian pediatrics 2000 542:998-1005 looked at the application of oils on newborns and concluded that topically applied oils can be absorbed into neonates is probably available for nutritional purposes.

In order for a butter to be of interest to the personal care market, it must be (1) soft at room temperature; (2) must not "crack" when handled; (3) must be able to be applied to the skin at ambient temperature by rubbing; (4) must liquefy upon rubbing, (5) must be free of rancidity and (6) must be free of trans acids that are the result of partial hydrogenation. For unsaturated oils to be made into butters, partial hydrogenation is the most common approach.

Prior to the current invention there has not been disclosed a butter for personal care applications that (1) is soft at room temperature; (2) does not "crack" when handled; (3) can be applied to the skin at ambient temperature by rubbing; (4) will liquefy upon rubbing, (5) will provide an aesthetically appealing feel when applied; (6) is free of rancidity and (7) is free of trans acids that are the result of partial hydrogenation.

THE INVENTION

Object of the Invention

It is the object of the present invention to provide a series of butters for personal care applications that (1) is soft at room temperature; (2) does not "crack" when handled; (3) can be applied to the skin at ambient temperature by rubbing; (4) will liquefy upon rubbing, (5) will provide an aesthetically appealing feel when applied; (6) is free of rancidity and (7) is free of trans acids that are the result of partial hydrogenation.

All temperatures reported herein are degrees Celsius, all percentages are percentages by weight, and all references are incorporated herein by reference where allowed.

SUMMARY OF THE INVENTION

It has been surprisingly found that totally randomized triglycerides with a very specific ratio of "R" groups provides a butter that (1) is soft at room temperature; (2) does not "crack" when handled; (3) can be applied to the skin at ambient temperature by rubbing; (4) will liquefy upon rubbing, (5) will provide an aesthetically appealing feel when applied; (6) is free of rancidity and (7) is free of trans acids that are the result of partial hydrogenation.

By totally randomized is meant that the fatty acids esterified by reaction with glycerin are premixed at low temperature then heated and reacted to provide no group specificity as to the hydroxyl group reacted. This is in stark contrast to the situation that is used by living organisms. Enzyme systems have total specificity because enzymes react very differently than the totally randomized product.

We have also found that a very specific range of very specific fatty groups are required to get the desired seven properties of cosmetic butters.

DETAILED DESCRIPTION OF THE INVENTION

A totally randomized trans fat free butter which conforms to the following structure:

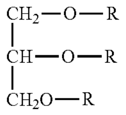

wherein:

R is a mixture of alkyl groups consisting of the group consisting of:

a. a first group selected from the group consisting of:

i. —C(O)—$(CH_2)_a$—$CH_3$ wherein;

a is an integer ranging from 6 to 8;

ii.

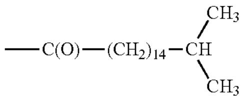

iii. and mixtures thereof b. a second group selected from the group consisting of:

i. —C(O)—$(CH_2)_b$—$CH_3$ wherein;

b is an even integer 16 to 18;

ii.

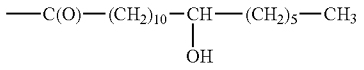

and iii. mixtures thereof;

and c. —C(O)—$(CH_2)_{20}$—$CH_3$ derived from behenic acid having the CAS number of 112-85-6.

In a preferred embodiment, the totally randomized trans free butter, which conforms to the following structure:

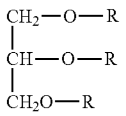

wherein:

R is a mixture of alkyl groups comprising:

a. between 1.45 and 2.6 moles of a first alkyl group selected from the group consisting of:

i. (—C(O)—$(CH_2)_a$—$CH_3$ wherein;

a is an even integer 6 to 8;

ii.

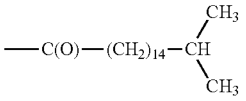

derived from isostearic acid and iii. mixtures thereof;

b. between 0.8 moles of 0.20 moles of a second alkyl group selected from the group consisting of;

i.

—C(O)—$(CH_2)_b$—$CH_3$ wherein;

b is an integer ranging from 16 to 18;

ii.

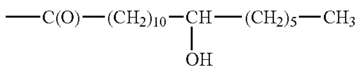

and iii. mixtures thereof;

and c. between 0.75 and 0.2 moles of —C(O)—$(CH_2)_{20}$—$CH_3$ derived from behenic acid having the CAS number of 112-85-6.

with the proviso that the total number of moles of (b)+(c) is less than 1.0.

A totally randomized butter, which is produced by the esterification reaction of a. glycerin which has the following structure:

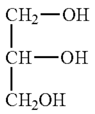

b. a first group of fatty acids selected from the group consisting of;

i. HO—C(O)—$(CH_2)_a$—$CH_3$ wherein;

a is an even integer 6 to 8;

ii.

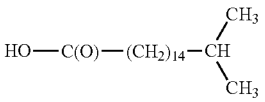

derived from isostearic acid and iii. mixtures thereof c. a second group of fatty acids selected from the group consisting of;

i. HO—C(O)—$(CH_2)_b$—$CH_3$ wherein;

b is an integer ranging from 16 to 18;

ii.

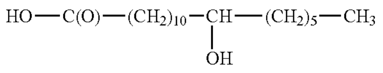

and iii. mixtures thereof;

and iv. HO—C(O)—$(CH_2)_{20}$—$CH_3$ having the CAS number of 112-85-6;

with the proviso that the total number of moles of (b)+(c) is less than 1.0;

and wherein said groups of fatty acids and glycerin are premixed and heated to produce a totally randomized product; said mixture is reacted at a temperature of between 150 and 150° C. until the acid value is reduced by 98%.

A totally randomized butter, which is produced by the esterification reaction of a. one mole of glycerin which has the following structure:

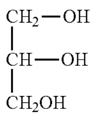

with b. between 1.45 and 2.6 moles of a first group of fatty acids selected from the group consisting of;

i. HO—C(O)—$(CH_2)_a$—$CH_3$ wherein;

a is an even integer 6 to 8;

ii.

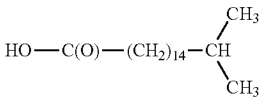

and iii. mixtures thereof;

c. between 0.2 and 0.8 moles of a second group of fatty acids selected from the group consisting of;

i. HO—C(O)—$(CH_2)_b$—$CH_3$ wherein;

b is an even integer 16 to 18;

ii.

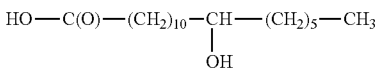

and iii. mixtures thereof;

and d. between 0.75 and 0.2 moles of HO—C(O)—$(CH_2)_{20}$—$CH_3$ with the proviso that the total number of moles of (b)+(c) is less than 1.0; wherein said groups of fatty acids and glycerin are premixed and heated to produce a totally randomized product; said mixture is reacted at a temperature of between 150 and 150° C. until the acid value is reduced by 98%.

If the butter is not carefully selected in that it is (a) totally randomized, (b) has the proper ratio of the proper fatty acids chosen for the synthesis and the proper mole ratio of fatty acids to glycerin, an unacceptable product will result. Additionally there are specific requirements that make the products of the present invention suitable for cosmetic application as butters. These include: (1) is soft at room temperature; (2) does not "crack" when handled; (3) can be applied to the skin at ambient temperature by rubbing; (4) will liquefy upon rubbing, (5) will provide an aesthetically appealing feel when applied; (6) is free of rancidity and (7) is free of trans acids that are the result of partial hydrogenation.

It must be clearly understood that the type and ratio of fatty acids reacted with glycerin and the fact that all items are premixed before reaction results in the desired totally randomized triglyceride is essential.

It must also be clearly understood that in the totally randomized esters made are complex compositions. A salient aspect of this invention is the behenic acid which requires between 0.75 and 0.2 moles of —C(O)—$(CH_2)_{20}$—$CH_3$. This means that on average there is less than 1 behenyl group on the molecule (actually 0.75) at the highest level and 0.2 of behenyl at the low end. The way to understand this is that of the 3 hydroxyl groups present only 0.6 have a behenyl at the lower limits. This means 2.4 have no behenyl at all. Operation out of this range produces unacceptable butters. This is indeed both surprising and quite unexpected. Too little behenic results if a product that is a semi solid not a butter, and too much results in a solid brittle hard wax.

Nature, using enzyme as described elsewhere in the application does not give this type of random system. Blending esters to the average composition (glyceryl tribehenate, glyceryl tri-isostearate and glyceryl tri stearate) produces failure butters as they lack the randomized aspect of the current invention.

PREFERRED EMBODIMENTS

In a preferred embodiment the ratio of the first group of fatty acids to the second group of fatty acids to behenic acid is 1.45:0.8:0.75.

In another preferred embodiment the ratio of the first group of fatty acids to the second group of fatty acids to behenic acid is 2.6:0.2:0.5.

In the most preferred embodiment the ratio of the first group of fatty acids to the second group of fatty acids to behenic acid is 2.0:0.5:0.5.

In a preferred embodiment a is 8.

In a preferred embodiment a is 6.

In a preferred embodiment b is 16.

In a preferred embodiment b is 18.

In a preferred embodiment the fatty acid from the second group of fatty acids is;

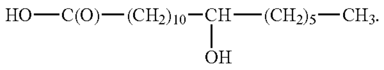

In a preferred embodiment the fatty acid selected from the first group is;

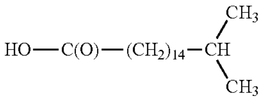

In a preferred embodiment b is 16 and a is 6.

In a preferred embodiment b is 18 and a is 8.

EXAMPLES

Example 1

Isostearic Acid

Isostearic Acid is an item of commerce, which has the following structure:

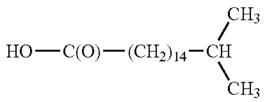

It has CAS number 30399-84-9 and a molecular weight: 284

It is an item of commerce, available from a number of supplier's including Sigma Aldrich.

Examples 2-3

Caprylic and capric acids are items of commerce. The structure is:

$$HO—C(O)—(CH_2)_a—CH_3$$

wherein;

a is an even integer 6 to 8;

| Example | a | Common Name | Structure | CAS | MW |
|---|---|---|---|---|---|
| 2 | 6 | Caprylic Acid | $CH_3(CH_2)_6COOH$ | 124-07-2 | 144 |
| 3 | 8 | Capric Acid | $CH_3(CH_2)_8COOH$ | 344-48-5 | 172 |

These fatty acids are items of commerce available from a variety of sources, most notable Cognis.

Example 4-6

Fatty Acids of the Present Invention $$HO—C(O)—(CH_2)_a—CH_3$$

wherein a is an integer ranging from 16 to 18.

These fatty acids are items of commerce available from a variety of sources, most notable Cognis.

| Example | a | Common Name | Structure | CAS | MW |
|---|---|---|---|---|---|
| 4 | 16 | Stearic acid | $CH_3(CH_2)_{16}COOH$ | 57-11-4 | 284 |
| 5 | 18 | Arachidic acid | $CH_3(CH_2)_{18}COOH$ | 506-30-9 | 312 |
| 6 | 12 | 12 hydroxystearic acid | $CH_3(CH_2)_5CH(OH)(CH_2)_{10}COOH$ | 106-14-9 | 300 |

Example 7

Behenic Acid $$HO—C(O)—(CH_2)_{20}—CH_3$$

wherein a is an integer ranging from 16 to 18.

Behenic acid is commerce available from a variety of sources, most notable Cognis. The CAS number is 112-85-6 and the molecular weight (MW) is 340.

Example 8-11

Fatty Acids Outside the Present Invention $$HO—C(O)—(CH_2)_a—CH_3$$

wherein a is less than 16 or greater than 20.

As will become clear those acids having "a" value less than 16 do not provide butters, but semisolids and those with "a" values above 20 provide brittle hard waxes, both of which are not suitable as cosmetic skin butters.

These fatty acids are items of commerce available from a variety of sources, most notable Cognis.

| Example | a | Common Name | Structure | CAS | MW |
|---|---|---|---|---|---|
| 8 | 22 | lignoceric acid | $CH_3(CH_2)_{22}COOH$ | 557-59-5 | 368 |
| 9 | 24 | cerotic acid | $CH_3(CH_2)_{24}COOH$ | 506-46-7 | 396 |
| 10 | 14 | palmitic acid | $CH_3(CH_2)_{14}COOH$ | 57-10-3 | 256 |
| 11 | 12 | myristic acid | $CH_3(CH_2)_{12}COOH$ | 544-63-8 | 228 |

Example 12

Glycerin

Glycerin is an item of commerce. It is available from a variety of manufacturers most notably Cognis. Glycerin has the CAS number 56-81-5. It has three hydroxyl groups, that are ultimately reacted with specific fatty acids.

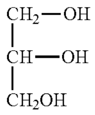

Glycerin has a molecular weight (MW) of 93.

Preparation of the Compounds of the Present Invention

General Procedure

In a suitable reaction flask with agitation, the ability to strip off water, thermometer and the ability to heat contents to between 150° C. and 180° C. is added the specified number of grams of glycerin (Example 12) is added the specified number of grams of the specified (a) group fatty acid. (Examples 1-3), next add the specified number of grams of the specified (b) group fatty acids (Example 4-6), followed by the specified number of grams of behenic acid (Example 7). Heat and agitation is applies and the reaction starts about 150° C.

Calculations

Examples 13-24 of the Present Invention

In order to make a triglyceride, the glycerin, which contains three hydroxyl groups needs to be reacted with three moles of fatty acids of the type specified Type 1 acid are example 1-3

Type 2 acids are example 4-6

Type 3 is behenic acid.

There is always 1 mole (3 hydroxyl groups) of glycerin.

The examples below show the number of grams needed to be added for each group.

Group 1 features the ratio of 1.45 Type 1:0.80 type 2 to 0.75 of type 3. This is the high ratio of type 1.

Group 1

Example 13

| Material | Example | MW | MR | MW * MR | % | Grams |
|---|---|---|---|---|---|---|
| Isostearic Acid | 1 | 284 | 1.45 | 411.80 | 41.7 | 104.31 |
| Stearic Acid | 4 | 284 | 0.80 | 227.20 | 23.0 | 57.55 |
| Behenic Acid | 7 | 340 | 0.75 | 255.00 | 25.8 | 64.59 |
| Glycerin | 12 | 93 | 1.00 | 93.00 | 9.4 | 23.56 |
| | | | | 987.00 | 100.0 | 250.00 |

Example 14

| Material | Example | MW | MR | MW * MR | % | Grams |
|---|---|---|---|---|---|---|
| Caprylic Acid | 2 | 144 | 1.45 | 208.80 | 25.9 | 64.73 |
| Arachadidic Acid | 5 | 312 | 0.80 | 249.60 | 31.0 | 77.38 |
| Behenic Acid | 7 | 340 | 0.75 | 255.00 | 31.6 | 79.06 |
| Glycerin | 12 | 93 | 1.00 | 93.00 | 11.5 | 28.83 |
| | | | | 806.40 | 100.0 | 250.00 |

Example 15

| Material | Example | MW | MR | MW * MR | % | Grams |
|---|---|---|---|---|---|---|
| Capric Acid | 3 | 172 | 1.45 | 249.40 | 30.2 | 75.61 |
| Stearic Acid | 4 | 284 | 0.80 | 227.20 | 27.6 | 68.88 |
| Behenic Acid | 7 | 340 | 0.75 | 255.00 | 30.9 | 77.31 |
| Glycerin | 12 | 93 | 1.00 | 93.00 | 11.3 | 28.20 |
| | | | | 824.60 | 100.0 | 250.00 |

Example 16

| Material | Example | MW | MR | MW * MR | % | Grams |
|---|---|---|---|---|---|---|
| isostearic Acid | 1 | 284 | 1.45 | 411.80 | 41.2 | 102.97 |
| 12 hydroxy stearic | 6 | 300 | 0.80 | 240.00 | 24.0 | 60.01 |
| Behenic Acid | 7 | 340 | 0.75 | 255.00 | 25.5 | 63.76 |
| Glycerin | 12 | 93 | 1.00 | 93.00 | 9.3 | 23.25 |
| | | | | 999.80 | 100.0 | 250.00 |

| Group 1 Summary | | Ratio |
|---|---|---|
| Acids | Type 1 | 1.45 |
| | Type 2 | 0.8 |
| | Behenic | 0.75 |
| Total Moles Acid | | 3 |
| Glycerin | | |
| Total OH moles | | 3 |

Group 2 features the ratio of 2.6 Type 1:0.20 type 2 to 0.2 of type 3. This is the low ratio of type 1.

Group 2

Example 17

| Material | Example | MW | MR | MW * MR | % | Grams |
|---|---|---|---|---|---|---|
| Isostearic Acid | 1 | 284 | 2.60 | 738.40 | 77.2 | 193.06 |
| Stearic Acid | 4 | 284 | 0.20 | 56.80 | 5.9 | 14.85 |
| Behenic Acid | 7 | 340 | 0.20 | 68.00 | 7.1 | 17.78 |
| Glycerin | 12 | 93 | 1.00 | 93.00 | 9.7 | 24.31 |
| | | | | 956.20 | 100.0 | 250.00 |

Example 18

| Material | Example | MW | MR | MW * MR | % | Grams |
|---|---|---|---|---|---|---|
| Caprylic Acid | 2 | 144 | 1.45 | 208.80 | 25.9 | 64.73 |
| Arachidic Acid | 5 | 312 | 0.80 | 249.60 | 31.0 | 77.38 |
| Behenic Acid | 7 | 340 | 0.75 | 255.00 | 31.6 | 79.06 |
| Glycerin | 12 | 93 | 1.00 | 93.00 | 11.5 | 28.83 |
| | | | | 806.40 | 100.0 | 250.00 |

Example 19

| Material | Example | MW | MR | MW * MR | % | Grams |
|---|---|---|---|---|---|---|
| Capric Acid | 3 | 172 | 1.45 | 249.40 | 30.2 | 75.61 |
| Stearic Acid | 4 | 284 | 0.80 | 227.20 | 27.6 | 68.88 |
| Behenic Acid | 7 | 340 | 0.75 | 255.00 | 30.9 | 77.31 |
| Glycerin | 12 | 93 | 1.00 | 93.00 | 11.3 | 28.20 |
| | | | | 824.60 | 100.0 | 250.00 |

Example 20

| Material | Example | MW | MR | MW * MR | % | Grams |
|---|---|---|---|---|---|---|
| isostearic Acid | 1 | 284 | 1.45 | 411.80 | 41.2 | 102.97 |
| 12 hydroxy stearic | 6 | 300 | 0.80 | 240.00 | 24.0 | 60.01 |
| Behenic Acid | 7 | 340 | 0.75 | 255.00 | 25.5 | 63.76 |
| Glycerin | 12 | 93 | 1.00 | 93.00 | 9.3 | 23.25 |
| | | | | 999.80 | 100.0 | 250.00 |

| | | Ratio |
|---|---|---|
| Acids | Type 1 | 2.6 |
| | Type 2 | 0.2 |
| | Behenic | 0.2 |
| Total Moles Acid | | 3 |
| Glycerin | | |
| Total OH Moles | | 3 |

Group 3 features the ratio of 2.0 Type 1:0.5 type 2 to 0.5 of type 3.

Group 3

Example 21

| Material | Example | MW | MR | MW * MR | % | Grams |
|---|---|---|---|---|---|---|
| Isostearic Acid | 1 | 284 | 2.00 | 568.00 | 58.4 | 145.94 |
| Stearic Acid | 4 | 284 | 0.50 | 142.00 | 14.6 | 36.49 |
| Behenic Acid | 7 | 340 | 0.50 | 170.00 | 17.5 | 43.68 |
| Glycerin | 12 | 93 | 1.00 | 93.00 | 9.6 | 23.90 |
| | | | | 973.00 | 100.0 | 250.00 |

Example 22

| Material | Example | MW | MR | MW * MR | % | Grams |
|---|---|---|---|---|---|---|
| Caprylic Acid | 2 | 144 | 2.00 | 288.00 | 40.7 | 101.84 |
| Arachidic Acid | 5 | 312 | 0.50 | 156.00 | 22.1 | 55.16 |
| Behenic Acid | 7 | 340 | 0.50 | 170.00 | 24.0 | 60.11 |
| Glycerin | 12 | 93 | 1.00 | 93.00 | 13.2 | 32.89 |
| | | | | 707.00 | 100.0 | 250.00 |

Example 23

| Material | Example | MW | MR | MW * MR | % | Grams |
|---|---|---|---|---|---|---|
| Capric Acid | 3 | 172 | 2.00 | 344.00 | 45.9 | 114.82 |
| Stearic Acid | 4 | 284 | 0.50 | 142.00 | 19.0 | 47.40 |
| Behenic Acid | 7 | 340 | 0.50 | 170.00 | 22.7 | 56.74 |
| Glycerin | 12 | 93 | 1.00 | 93.00 | 12.4 | 31.04 |
| | | | | 749.00 | 100.0 | 250.00 |

Example 24

| Material | Example | MW | MR | MW * MR | % | Grams |
|---|---|---|---|---|---|---|
| isostearic Acid | 1 | 284 | 2.00 | 568.00 | 57.9 | 144.75 |
| 12 hydroxy stearic | 6 | 300 | 0.50 | 150.00 | 15.3 | 38.23 |
| Behenic Acid | 7 | 340 | 0.50 | 170.00 | 17.3 | 43.32 |
| Glycerin | 12 | 93 | 1.00 | 93.00 | 9.5 | 23.70 |
| | | | | 981.00 | 100.0 | 250.00 |

| | | Ratio |
|---|---|---|
| Acids | Group 1 | 2 |
| | Group 2 | 0.5 |
| | Behenic | 0.5 |
| Total Moles Acid | | 3 |
| Glycerin | | |
| total OH moles | | 3 |

Calculations

Examples 25 Comparative Examples

In order to make a triglyceride, the glycerin, which contains three hydroxyl groups needs to be reacted with three moles of fatty acids of the type specified.

Type 1 acid are example 1-3

Type 2 acids (example 4-6) have been replaced with acids

Examples 8-11 outside the claimed range

Type 3 is behenic acid.

As before there is always 1 mole (3 hydroxyl groups) of glycerin.

The examples below show the number of grams needed to be added for each group.

Preparation of the Compounds of Outside the Present Invention

General Procedure

In a suitable reaction flask with agitation, the ability to strip off water, thermometer and the ability to heat contents to between 150° C. and 180° C. is added the specified number of grams of glycerin (Example 12) is added the specified number of grams of the specified (a) group fatty acid. (Examples 1-3), next add the specified number of grams of the specified (b) group of fatty acids outside the scope of the present invention, i.e. fatty acids (Example 8-11), followed by the specified number of grams of behenic acid (Example 7). Heat and agitation is applies and the reaction starts about 150° C.

Group 4

Example 25

| Material | Example | MW | MR | MW * MR | % | Grams |
|---|---|---|---|---|---|---|
| Isostearic Acid | 1 | 284 | 1.5 | 411.8 | 39.1 | 97.7 |
| Lignoceric Acid | 9 | 368 | 0.8 | 294.4 | 27.9 | 69.8 |
| Behenic Acid | 7 | 340 | 0.8 | 255.0 | 24.2 | 60.5 |
| Glycerin | 12 | 93 | 1.0 | 93.0 | 8.8 | 22.1 |
| | | | | 1054.2 | 100.0 | 250.0 |

Product is not a wax. Hard brittle solid.

Example 26

| Material | Example | MW | MR | MW * MR | % | Grams |
|---|---|---|---|---|---|---|
| Caprylic Acid | 2 | 144 | 1.5 | 208.8 | 23.9 | 59.8 |
| Cerotic Acid | 9 | 396 | 0.8 | 316.8 | 36.3 | 90.7 |
| Behenic Acid | 7 | 340 | 0.8 | 255.0 | 29.2 | 73.0 |
| Glycerin | 12 | 93 | 1.0 | 93.0 | 10.6 | 26.6 |
| | | | | 873.6 | 100.0 | 250.0 |

Product is not a wax. Hard brittle solid.

Example 27

| Material | Example | MW | MR | MW * MR | % | Grams |
|---|---|---|---|---|---|---|
| Capric Acid | 3 | 172 | 1.5 | 249.4 | 31.1 | 77.7 |
| Palmitic Acid | 10 | 256 | 0.8 | 204.8 | 25.5 | 63.8 |
| Behenic Acid | 7 | 340 | 0.8 | 255.0 | 31.8 | 79.5 |
| Glycerin | 12 | 93 | 1.0 | 93.0 | 11.6 | 29.0 |
| | | | | 802.2 | 100.0 | 250.0 |

Product is slushy, not a butter

Example 28

| Material | Example | MW | MR | MW * MR | % | Grams |
|---|---|---|---|---|---|---|
| isostearic Acid | 1 | 284 | 1.5 | 411.8 | 43.7 | 109.3 |
| Myristic Acid | 11 | 228 | 0.8 | 182.4 | 19.4 | 48.4 |
| Behenic Acid | 7 | 340 | 0.8 | 255.0 | 27.1 | 67.7 |
| Glycerin | 12 | 93 | 1.0 | 93.0 | 9.9 | 24.7 |
| | | | | 942.2 | 100.0 | 250.0 |

Product is slushy.

Group 5

Example 29

| Material | Example | MW | MR | MW * MR | % | Grams |
|---|---|---|---|---|---|---|
| Isostearic Acid | 1 | 284 | 2.60 | 738.40 | 75.5 | 188.64 |
| Cerotic Acid | 9 | 396 | 0.20 | 79.20 | 8.1 | 20.23 |
| Behenic Acid | 7 | 340 | 0.20 | 68.00 | 6.9 | 17.37 |
| Glycerin | 12 | 93 | 1.00 | 93.00 | 9.5 | 23.76 |
| | | | | 978.60 | 100.0 | 250.00 |

Product hard, brittle wax.

Example 30

| Material | Example | MW | MR | MW * MR | % | Grams |
|---|---|---|---|---|---|---|
| Caprylic Acid | 2 | 144 | 1.45 | 208.80 | 23.9 | 59.75 |
| Lignoceric Acid | 9 | 396 | 0.80 | 316.80 | 36.3 | 90.66 |
| Behenic Acid | 7 | 340 | 0.75 | 255.00 | 29.2 | 72.97 |
| Glycerin | 12 | 93 | 1.00 | 93.00 | 10.6 | 26.61 |
| | | | | 873.60 | 100.0 | 250.00 |

Hare Brittle wax

Example 31

| Material | Example | MW | MR | MW * MR | % | Grams |
|---|---|---|---|---|---|---|
| Capric Acid | 3 | 172 | 1.45 | 249.40 | 31.1 | 77.72 |
| Palmitic Acid | 10 | 256 | 0.80 | 204.80 | 25.5 | 63.82 |
| Behenic Acid | 7 | 340 | 0.75 | 255.00 | 31.8 | 79.47 |
| Glycerin | 12 | 93 | 1.00 | 93.00 | 11.6 | 28.98 |
| | | | | 802.20 | 100.0 | 250.00 |

Soft Slush

Example 32

| Material | Example | MW | MR | MW * MR | % | Grams |
|---|---|---|---|---|---|---|
| isostearic Acid | 1 | 284 | 1.45 | 411.80 | 43.7 | 109.27 |
| Myristic Acid | 11 | 228 | 0.80 | 182.40 | 19.4 | 48.40 |
| Behenic Acid | 7 | 340 | 0.75 | 255.00 | 27.1 | 67.66 |
| Glycerin | 12 | 93 | 1.00 | 93.00 | 9.9 | 24.68 |
| | | | | 942.20 | 100.0 | 250.00 |

Soft slush

Group 6

Example 33

| Material | Example | MW | MR | MW * MR | % | Grams |
|---|---|---|---|---|---|---|
| Isostearic Acid | 1 | 284 | 2.00 | 568.00 | 59.2 | 148.07 |
| Palmitic Acid | 10 | 256 | 0.50 | 128.00 | 13.3 | 33.37 |
| Behenic Acid | 7 | 340 | 0.50 | 170.00 | 17.7 | 44.32 |
| Glycerin | 12 | 93 | 1.00 | 93.00 | 9.7 | 24.24 |
| | | | | 959.00 | 100.0 | 250.00 |

Soft Slush

Example 34

| Material | Example | MW | MR | MW * MR | % | Grams |
|---|---|---|---|---|---|---|
| Caprylic Acid | 2 | 144 | 2.00 | 288.00 | 39.2 | 97.96 |
| Lignoceric Acid | 8 | 368 | 0.50 | 184.00 | 25.0 | 62.59 |

-continued

| Material | Example | MW | MR | MW * MR | % | Grams |
|---|---|---|---|---|---|---|
| Behenic Acid | 7 | 340 | 0.50 | 170.00 | 23.1 | 57.82 |
| Glycerin | 12 | 93 | 1.00 | 93.00 | 12.7 | 31.63 |
| | | | | 735.00 | 100.0 | 250.00 |

Hard wax

Example 35

| Material | Example | MW | MR | MW * MR | % | Grams |
|---|---|---|---|---|---|---|
| Capric Acid | 3 | 172 | 2.00 | 344.00 | 42.7 | 106.83 |
| Cerotic Acid | 9 | 396 | 0.50 | 198.00 | 24.6 | 61.49 |
| Behenic Acid | 7 | 340 | 0.50 | 170.00 | 21.1 | 52.80 |
| Glycerin | 12 | 93 | 1.00 | 93.00 | 11.6 | 28.88 |
| | | | | 805.00 | 100.0 | 250.00 |

Hard wax

Example 36

| Material | Example | MW | MR | MW * MR | % | Grams |
|---|---|---|---|---|---|---|
| isostearic Acid | 1 | 284 | 2.00 | 568.00 | 60.1 | 150.26 |
| Myristic Acid | 11 | 228 | 0.50 | 114.00 | 12.1 | 30.16 |
| Behenic Acid | 7 | 340 | 0.50 | 170.00 | 18.0 | 44.97 |
| Glycerin | 12 | 93 | 1.00 | 93.00 | 9.8 | 24.60 |
| | | | | 945.00 | 100.0 | 250.00 |

soft slush

As can clearly been seen from the above data, there is a very specific range of very specific types and ratios of fatty acids to glycerin to provide the highly desirable cosmetic butter. In order for a butter to be of interest to the personal care market, it must be (1) soft at room temperature; (2) must not "crack" when handled; (3) must be able to be applied to the skin at ambient temperature by rubbing; (4) must liquefy upon rubbing, (5) must be free of rancidity and (6) must be free of trans acids that are the result of partial hydrogenation. For unsaturated oils to be made into butters, partial hydrogenation is the most common approach.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A totally randomized butter produced by the esterification reaction of:

a. glycerin which has the following structure:

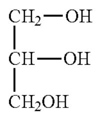

and b. a first group of fatty acids selected from the group consisting of i. $HO—C(O)—(CH_2)_a—CH_3$ wherein;

a is an even integer 6 to 8;

ii. isostearic acid with the structure of:

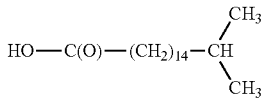

and mixtures thereof;

c. a second group of fatty acid of selected from the group consisting of;

i. $HO—C(O)—(CH_2)_b—CH_3$ wherein b is 16 to 18;

ii. 12-hydroxyl stearic acid having the structure of:

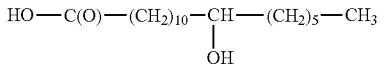

and mixtures thereof;

and d. behenic acid having the following structure:

$HO—C(O)—(CH_2)_{20}—CH_3$ with the proviso that the total number of moles of (b)+(c) is less than 1.0.

2. The totally randomized triglyceride of claim 1 wherein said groups of fatty acids and glycerin are premixed and heated to produce a totally randomized product; said mixture is reacted at a temperature of between 150 and 180° C. until the acid value is reduced by 98%.

3. The totally randomized triglyceride of claim 1 wherein the fatty acid from the first group is isostearic acid.

4. The totally randomized triglyceride of claim 1 wherein a is 8.

5. The totally randomized triglyceride of claim 1 wherein a is 6.

6. The totally randomized triglyceride of claim 1 wherein b is 16.

7. The totally randomized triglyceride of claim 1 wherein b is 18.

8. The totally randomized triglyceride of claim 1 wherein the fatty acid from the second group of fatty acids of is 12-hydroxystearic acid.

9. The totally randomized triglyceride of claim 7 wherein the ratio of the first group of fatty acids to the second group of fatty acids to behenic acid is 1.45:0.8:0.75.

10. The totally randomized triglyceride of claim 7 wherein the ratio of the first group of fatty acids to the second group of fatty acids to behenic acid is 2.6:0.2:0.5.

11. The totally randomized triglyceride of claim 7 wherein the ratio of the first group of fatty acids to the second group of fatty acids to behenic acid is 2.0:0.5:0.5.

12. The totally randomized triglyceride of claim 7 wherein a is 8.

13. The totally randomized triglyceride of claim 7 wherein a is 6.

14. The totally randomized triglyceride of claim 7 wherein b is 16.

15. The totally randomized triglyceride of claim 7 wherein b is 18.

16. The totally randomized triglyceride of claim 10 wherein the fatty acid form the second group of fatty acids is;

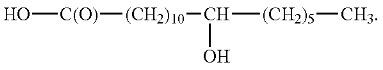

17. The totally randomized triglyceride of claim 10 wherein a is 8.

18. The totally randomized triglyceride of claim 10 wherein a is 6.

19. The totally randomized triglyceride of claim 10 wherein b is 16.

20. The totally randomized triglyceride of claim 10 wherein the fatty acid of group 2 Is:

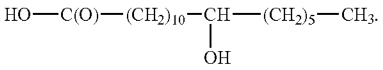

* * * * *